United States Patent [19]

Köcher et al.

[11] Patent Number: 5,128,267
[45] Date of Patent: Jul. 7, 1992

[54] NAPHTHOTRIAZOLIUM SALTS

[75] Inventors: Jürgen Köcher, Cologne; Meinhard Rolf, Leverkusen; Klaus Wehling, Wuppertal, all of Fed. Rep. of Germany

[73] Assignee: Miles Inc., Elkhart, Ind.

[21] Appl. No.: 656,711

[22] Filed: Feb. 19, 1991

[30] Foreign Application Priority Data

Mar. 7, 1990 [DE] Fed. Rep. of Germany ...... 4007 058

[51] Int. Cl.$^5$ ........................................... C07D 417/04
[52] U.S. Cl. ...................................... 436/92; 548/129; 548/138; 548/159; 548/181; 548/212; 548/214; 548/257; 548/260
[58] Field of Search ............... 548/129, 138, 159, 181, 548/212, 214, 257, 260; 436/92

Primary Examiner—Robert Gerstl
Attorney, Agent, or Firm—Andrew L. Klawitter; Jerome L. Jeffers

[57] ABSTRACT

Naphthotriazolium salts which are chromogenic indicators for reducing substrate, such as NADH or NADPH.

7 Claims, No Drawings

NAPHTHOTRIAZOLIUM SALTS

BACKGROUND OF THE INVENTION

The present invention relates to naphthotriazolium salts, their synthesis and use in the determination of reducing substances.

The present triazolium salts are usually colorless or weakly yellow compounds which upon reduction are converted into azo dyes (R. Kuhn and E. Ludolphy, Liebigs, Ann. Chem. 564, 35–43, (1949). Accordingly, the present compounds are useful for the quantitative determination of reducing substances by photometric methods, e.g., by measuring absorbance or reflectance. A field of application of interest is, for example, the quantitative detection of reducing gases in the atmosphere. Such compounds can be, for example, $H_2S$, $AsH_3$, $B_2H_6$ or $PH_3$. Moreover, other reducing substances can also be detected by reaction with the naphthotriazolium salts of the present invention, for example, organic thiols, ascorbic acid, and biological reducing agents such as NADH or NADPH.

It is well known that reducing pyridine nucleotides react in the presence of N-methyl-phenazinium salts or the enzyme diaphorase with reduction indicators such as, for example, the tetrazolium salts to give colored products (H.U. Bergmeyer, Methods of Enzymatic Analysis, 3rd edition, Vol. I, p. 197 et seq.). A number of assay methods for reduced pyridine nucleotides such as NADH or NADPH are based on these reactions. In the presence of the enzyme diaphorase, NADH reduces a reductive indicator, such as a tetrazolium salt, with the formation of AND to give a dye whose concentration can be determined by a variety of photometric means. By coupling this indicator reaction with various enzymatic redox reactions, a variety of different analytes, for example glucose or cholesterol, can be determined in body fluids.

Triazolium salts, as opposed to the well-known tetrazolium salts, have been suggested for use in the determination of NADH, however, from the literature they are known to have inferior reducibility compared to the tetrazolium salts, and are therefore too slowly reacting [E. Seidler, Acta Histochem. 82, 89–93 (1987)]. Furthermore, in the case of the triazolium salts described in the literature, the absorption maxima of the reduction products are of very short wavelength ($\lambda$ max <540 nm). Indicators producing dye products compounds having distinctly longer wavelength absorption maxima are desirable in order, for example, to be able to carry out measurements free of hemoglobin or bilirubin interferences.

It is an object of the present invention to provide triazolium salts characterized by easy and rapid reducibility and bathochromic absorption maxima, and which are thus advantageous for use in the chromogenic determination of reducing substances, particularly NADH.

SUMMARY OF THE INVENTION

It has been found that the hitherto unknown naphthotriazolium salts of formula I, substituted by heterocycles, are rapidly and easily reducible and are distinguished by particularly bathochromic absorption spectra:

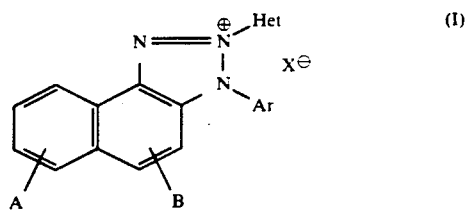

wherein A and B, independently of one another, are selected from the following substituents: hydrogen, alkyl having 1 to 4 carbon atoms such as methyl, ethyl, propyl, isopropyl or butyl; alkoxy having 1 to 4 carbon atoms such as methoxy, ethoxy, propoxy, isopropoxy or butoxy, acylamino having 1 to 8 carbon atoms such as acetylamino, propionylamino or benzoylamino, amino, alkylamino having 1 to 4 carbon atoms such as methylamino, ethylamino, propylamino, isopropylamino or butylamino, phenylamino, N,N-di-$\beta$-hydroxyethylamino, N,N-di-$\beta$-sulfatoethylamino, sulfobenzylamino, N,N-disulfobenzylamino, alkoxycarbonyl having 1 to 4 carbon atoms in the alkoxy radical such as methoxycarbonyl or ethoxycarbonyl, alkylsulfonyl having 1 to 4 carbon atoms such as methylsulfonyl or ethylsulfonyl, trifluoromethyl, nitro, cyano, halo such as fluoro, chloro or bromo, carbamoyl, N-alkylcarbamoyl having 1 to 4 carbon atoms in the alkyl radical such as N-methylcarbamoyl or N-ethylcarbamoyl, sulfamoyl, N-alkylsulfamoyl having 1 to 4 carbon atoms such as N-methylsulfamoly, N-propylsulfamoyl, N-isopropylsulfamoyl or N-butylsulfamoyl, N-(4-hydroxyethyl)sulfamoyl, N,N-di($\beta$-hydroxyethyl)sulfamoyl, N-phenylsulfamoyl, ureido, hydroxyl, carboxyl, sulfomethyl or sulfo, Ar is an aromatic or heteroaromatic radical, Het is a radical of a heterocyclic diazonium compound, and $X^{\ominus}$ is a mono- or polyvalent organic or inorganic counteranion.

It is particularly preferred that Het be selected from the heterocyclic residues thiazolyl, benzothiazolyl, isothiazolyl, benzisothiazolyl, 1,2,4-thiadiazolyl, 1,3,4-thiadiazolyl and thiophenyl, which residues are unsubstituted or substituted with a group, normally a single group, selected from those recited above for A and B. Particularly useful are the heterocyclic residues shown in the structures in Table 1 below, namely, 2-benzothiazolyl, 3-benzisothiazolyl, and 2-(1,3,4-thiadiazolyl), and especially where A and B are both hydrogen and Ar is phenyl or nitro-substituted phenyl.

The group Ar is preferably of the formula:

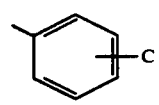

wherein C is selected from those substituents recited above for A and B, or is a fused carbocyclic or heterocyclic ring, e.g., a 5–8 membered ring.

DESCRIPTION OF THE PREFERRED EMBODIMENTS

The indicator compounds of the present invention are prepared by the known reaction of an optionally substituted N-aryl-2-naphthylamine of formula III

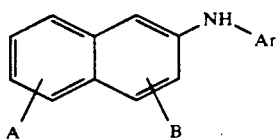

with a diazotized heterocyclic amine, and subsequent oxidation of the resulting azo dye of formula IV

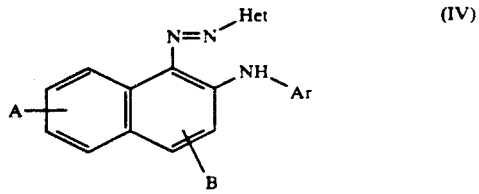

to give compounds of formula I. Suitable oxidizing agents for treatment of compound (IV) are, for example, Pb(OAc)$_4$, N-bromosuccinimide and iso-amyl nitrite.

The counteranion X can be modified in a subsequent step by suitable methods such as, for example, anion exchange chromatography, in order to obtain desired solubility. Useful counteranions include, without limitation, F$^\ominus$, Cl$^\ominus$, Br$^\ominus$, NO$_2^\ominus$, BF$_4^\ominus$, CH$_3$COO$^\ominus$, CF$_3$COO$^\ominus$, HSO$_4^\ominus$, SO$_4$ , alkylsulfonates, substituted alkylsulfonates, arylsulfonates and substituted arylsulfonates.

Starting compounds (III) are prepared in a known manner, for example by fusion of β-naphthols with aromatic amines.

The indicator compounds of the present invention are useful in the determination of reducing substances, and are particularly advantageous in assays based on NADH-dependent reactions. Representative of such NADH-dependent reactions are those catalyzed by the enzymes: lactate dehydrogenase, alcohol dehydrogenase, glucose dehydrogenase, glyceraldehyde dehydrogenase, glycerol phosphate dehydrogenase, and malate dehydrogenase. NADH can also be determined as the final product of multi-step enzymatic reactions as in the assay of glutamate oxalacetate transaminase (EC 2.6.11), glutamate pyruvate transaminase (EC2.6.12) or, alternatively, creatinine kinase (EC 2.7.32).

The present triazolium salt indicators can be comprised in a variety of test agents or test systems. Such test compositions can be in the form of a liquid reagent or in a solid form such as a powder (e.g., lyophilized) tablet, reagent strip, or the like. In addition to the indicator, such test compositions will generally comprise other reagents useful in the respective analysis, such as enzymes, substrates, coenzymes, effectors, antigens, antibodies, etc. Furthermore, such test compositions, agents and devices can also comprise non-reactive substances, such as buffers, wetting agents and stabilizer.

For so-called wet chemistry analysis, the test composition is used as a liquid or as a solid which is dissolvable in water or another suitable solvent to provide a reagent solution. Where the reagent consists of individual components, such can be mixed together to form a final reaction volume. After mixing the sample (for example, substrate solution, enzyme solution, blood, serum, plasma or urine) with an aliquot of the reagent, the resulting color is measured in a photometer and the respective analyte concentration is calculated by means of the molar extinction coefficients and the reagent or sample volumes added. Both kinetic and end point measurements can be performed.

The test composition can also be incorporated with a carrier matrix in the form of a reagent strip. Suitable carrier matrices are known in the art and include absorbent papers, woven and nonwoven cloth, glass fiber filters, polymeric membranes and films. Incorporation methods include impregation of a formed carrier matrix with a solution, suspension, or other liquid form of the test composition, in one or more steps, followed by drying of the matrix; and formation of a matrix in the presence of one or more of the components of the test composition, e.g., by casting or layering solutions of film or membrane forming formulations. As a further example, one or more impregnating solutions can be prepared in the form of aqueous or organic or mixed solutions, depending on solubilities and compatabilities of the reagents and auxiliary ingredients. Absorbent or swellable carriers such as filter paper or absorbent glass fiber filters or synthetic nonwovens are impregnated or sprayed with these solutions and then dried. The test composition can also be incorporated with carrier matrices which have been prepared from casting solutions. Cellulose, cellulose derivatives, gelatin, gelatin derivatives or, alternatively, porous plastics such as polyurethane and acrylamide may be mentioned by way of example.

Reagent strips can be employed as a rapid diagnostic for the direct determination of constituents of fluids (for example body fluids such as blood, urine or saliva, or in foodstuffs, for example fruit juices, milk and the like). The test liquid is usually applied directly to the reagent carrier or the carrier is briefly immersed in the fluid. A semi-quantitative determination is possible by relating the color thus formed to a color chart. A quantitative assay can be carried out by measurement of reflectance.

Suitable buffers for the test composition of the present invention, without limitation, are phosphates, citrates, borates and GOOD buffers having alkali metal or ammonium counterions. Desirable pH values are generally from about 5 to about 10, more preferably from about 6.5 to about 7.5.

Useful wetting agents are, without limitation, anionic and cationic wetting agents which interact ionically with the indicators of the invention. Non-ionic wetting agents which activate enzymes, however, can also be used. Sodium lauryl sulfate, dioctyl sodium sulfosuccinate and alkylaryl polyether alcohols are generally preferred.

Other auxiliary substances which can be comprised in the test composition are typical thickeners, solubilizers, emulsifiers, optical brighteners, contrast agents, etc., as are known in corresponding tests with other chromogens.

The invention will now be illustrated, but is not intended to be limited, by the following examples.

EXAMPLES 4.3 g of 2-aminobenzothiazole (0.029 mol) are introduced into a mixture of 40 ml of 85% strength H$_3$PO$_4$ and 20 ml of acetic acid. 10 ml (0.029 mol) of nitrosylsulphuric acid are added dropwise to is mixture at 0°–5° C. and the mixture is subsequently stirred at 0° C. for 4 hours. The diazonium salt solution thus obtained is added at 0°–5° C. in portions to a solution of 6.4 g of N-phenyl-2-naphthylamine (0.029 mol) in 200 ml of ethanol. The mixture is subsequently stirred at 10° C. for 2 hours and the precipitated reaction product is filtered off with suction. After washing with H₂O, 10.5 g of the azo dye of formula (V) are obtained.

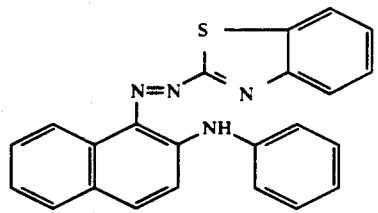
(V)

6 g of the above azo dye (0.016 mol) are initially introduced into 320 ml of acetic acid. The mixture is warmed to 50° C. and 2.6 ml of iso-amyl nitrite (0.020 mol) are added at this temperature. After stirring at 50° C. for 1 hour, the oxidation is complete. The warm solution is filtered to remove insoluble constituents and the acetic acid is distilled off in a water jet vacuum. The oil which remains is taken up in acetonitrile and the product formed is precipitated by addition of diethyl ether. 3 g of the triazolium salt of formula (VI) are obtained.

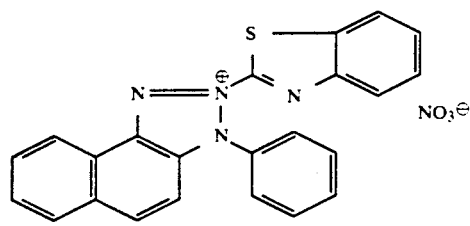
(VI)

The structure of this product is confirmed by mass spectroscopy (FAB). The counterion can be modified, for example, by exchange chromatography.

Other triazolium salts, for example having the structures 2-10 shown in Table 1, can be obtained in an analogous manner.

Optical properties of the indicators for the detection of NADH

The procedure for testing the optical and kinetic properties is as follows:

20 μl of diaphorase solution (200 kU/1) and 20 μl of a solution (usually 20 mmol/1) of the indicator to be tested are added in a suitable solvent to 2 ml of buffer solution (100 mmol/1, pH 4.7 or 9) in a measuring cuvette. The absorbance of the blank of this solution is determined. The reaction is then started by addition of 20 μl of NADH (5 mmol/1), and after 5 minutes the absorbance is measured against the blank.

In the case of the indicators tested, the end point of the reaction is attained within at most 2.5 minutes.

Buffer used (100 mmol/1): pH 5 citric acid-NaOH; pH 7 and pH 9: tris-hydroxymethylaminomethane HCl.

Table 1 which follows shows the optical and kinetic characteristics of the compounds according to the invention.

The present invention has been particularly described and exemplified above. Clearly, other variations and modifications of the invention can be made without departing from the spirit and scope hereof.

TABLE 1

| Example | Structure | $\lambda_{max}$ (nm) | $\epsilon(\lambda_{max})$ | End point (mm) |
|---|---|---|---|---|
| 1 | 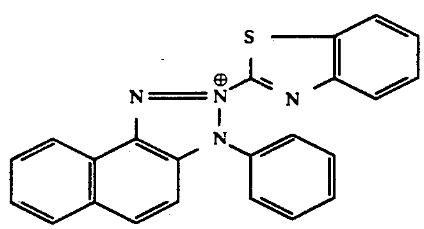 | 551 | 2200 | 0.5 |
| 2 | 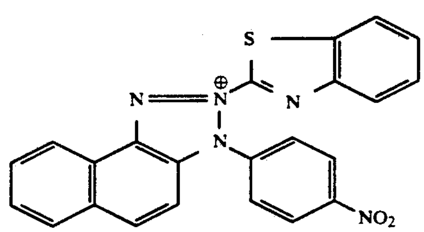 | 555 | 12300 | 0.5 |

TABLE 1-continued

| Example | Structure | $\lambda_{max}$ (nm) | $c(\lambda_{max})$ | End point (mm) |
|---|---|---|---|---|
| 3 | 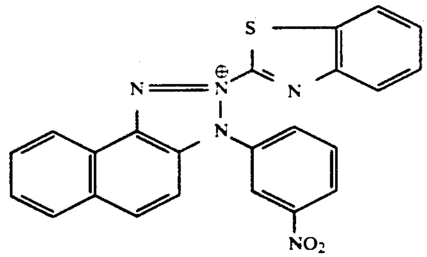 | 544 | 7780 | 2 |
| 4 | 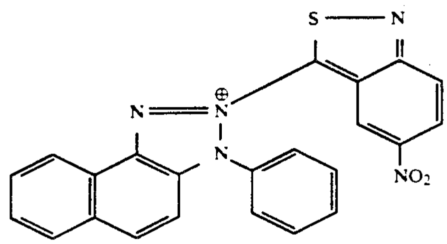 | 626 | 5480 | 1 |
| 5 | 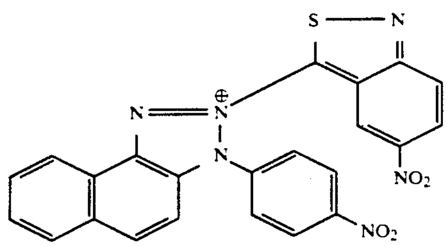 | 620 | 11220 | 2.5 |
| 6 | 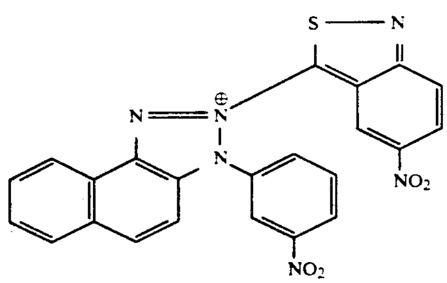 | 606 | 10320 | 1 |
| 7 | 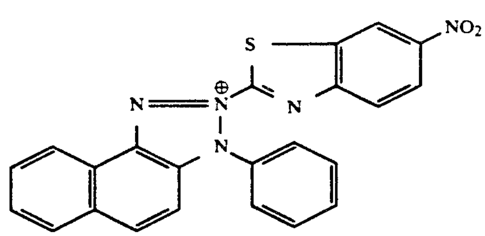 | 571 | 14040 | 2 |
| 8 | 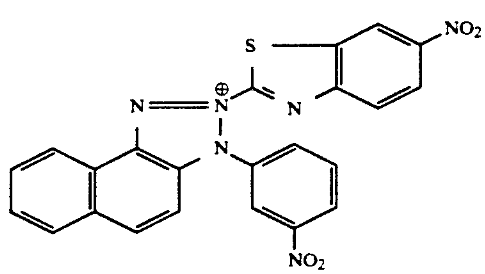 | 566 | 21180 | 2 |

TABLE 1-continued

| Example | Structure | $\lambda_{max}$ (nm) | $c(\lambda_{max})$ | End point (mm) |
|---|---|---|---|---|
| 9 | 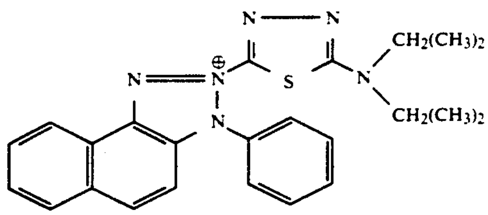 | 540 | 5700 | 2 |
| 10 | 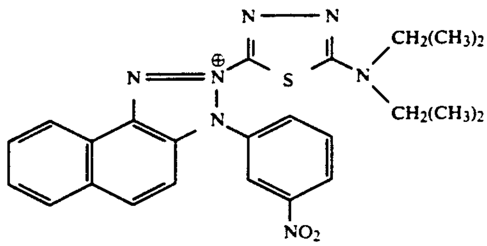 | 540 | 12820 | 1 |

What is claimed is:

1. Naphthotriazolium salts of the formula:

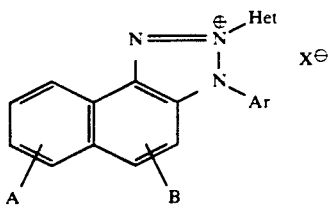

where A and B, independently of one another, are hydrogen, alkyl having 1 to 4 carbon atoms, alkoxy having 1 to 4 carbon atoms, acylamino having 1 to 8 carbon atoms, alkoxycarbonyl having 1 to 4 carbon atoms in the alkoxy radical, alkylsulfonyl having 1 to 4 carbon atoms, trifluoromethyl, nitro, cyano, halo, carbamoyl, N-alkylcarbamoyl having 1 to 4 carbon atoms in the alkyl radical, sulfamoyl, N-alkylsulfamoyl having 1 to 4 carbon atoms, N-(4-hydroxyethyl)-sulfamoyl, N,N-di-($\beta$-hydroxyethyl)sulfamoyl, N-phenylsulfamoyl, ureido, carboxyl, sulfomethyl or sulfo; Ar is an aromatic radical of the formula:

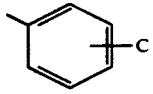

wherein C is selected from hydrogen, alkyl having 1 to 4 carbon atoms, alkoxy having 1 to 4 carbon atoms, acylamino having 1 to 8 carbon atoms, alkoxycarbonyl having 1 to 4 carbon atoms in the alkoxy radical, alkylsulfonyl having 1 to 4 carbon atoms, trifluoromethyl, nitro, cyano, halo, carbamoyl, N-alkylcarbamoyl having 1 to 4 carbon atoms in the alkyl radical, sulfamoyl, N-alkylsulfamoyl having 1 to 4 carbon atoms, N-(4-hydroxyethyl)sulfamoyl, N,N-di-($\beta$-hydroxyethyl)sulfamoyl, N-phenylsulfamoyl, ureido, carboxyl, sulfomethyl or sulfo or C is a 5-8 membered fused carbocyclic or heterocyclic ring; Het is selected from the group consisting of a heterocyclic residue of thiazolyl, benzothiazolyl, isothiazolyl, benzoisothiazolyl, 1,2,4-thiadiazolyl and 1,3,4-thiadiazolyl; and $X^\ominus$ is a mono or polyvalent organic or inorganic counteranion.

2. The traizolium salts of claim 1 wherein Het is unsubstituted or substituted with alkyl having 1 to 4 carbon atoms, alkoxy having 1 to 4 carbon atoms, acylamino having 1 to 8 carbon atoms, amino, alkylamino having 1 to 4 carbon atoms, phenylamino, N,N-di-$\beta$-hydroxyethylamino, N,N-di-$\beta$-sulfatoethylamino, sulfobenzylamino, N,N-disulfobenzylamino, alkoxycarbonyl having 1 to 4 carbon atoms in the alkoxy radical, alkylsulfonyl having 1 to 4 carbon atoms, trifluoromethyl, nitro, cyano, halo, carbamoyl, N-alkylcarbamoyl having 1 to 4 carbon atoms in the alkyl radical, sulfamoyl, N-alkylsulfamoyl having 1 to 4 carbon atoms, N-(4-hydroxyethyl)sulfamoyl, N,N-di-($\beta$-hydroxyethyl)sulfamoyl, N-phenylsulfamoyl, ureido, hydroxyl, carboxyl, sulfomethyl or sulfo.

3. The triazolium salts of claim 1 wherein Het is a 2-benzothiazolyl, 3-benzisothiazolyl, or 2-(1,3,4-thiadiazolyl) radical.

4. The triazolium salts of claim 3 wherein A and B are both hydrogen and Ar is phenyl or nitro-substituted phenyl.

5. The traizolium salts of claim 1 wherein $X^\ominus$ is $F^\ominus$, $Cl^\ominus$, $Br^\ominus$, $NO_2^\ominus$, $NO_3^\ominus$, $BF_4^\ominus$, $CH_3COO^\ominus$, $CF_3COO^\ominus$, $HSO_4$ , $SO_4^\ominus$, an alkylsulfonate, a substituted alkylsulfonate, an arylsulfonate, or substituted arylsulfonate.

6. A method for determining a reducing substance in an aqueous test sample, comprising the steps of contacting said test sample with a naphthotrizaolium salt indicator of any one of claims 1-5 and measuring the resulting color change.

7. The method of claim 6 wherein said reducing substance is NADH.

* * * * *